US00PP10332P

United States Patent [19]

Krans et al.

[11] Patent Number: Plant 10,332

[45] Date of Patent: Apr. 14, 1998

[54] 'MS-CHOICE' BERMUDAGRASS

[75] Inventors: Jeffrey V. Krans; H. Wayne Philley, both of Mississippi State, Miss.

[73] Assignee: Mississippi State University, Mississippi State, Mich.

[21] Appl. No.: 582,962

[22] Filed: Jan. 4, 1996

[51] Int. Cl.[6] ..... A01H 5/00

[52] U.S. Cl. ..... Plt./90

[58] Field of Search ..... Plt./90

[56] References Cited

U.S. PATENT DOCUMENTS

P.P. 6,278 9/1988 McMaugh et al. ..... Plt./90

OTHER PUBLICATIONS

Krans, J.V., et al. 1995 "Registration of 'MS–Choice' Bermudagrass" *Crop Science*, vol. 35, Sep.–Oct., p. 1506.

*Primary Examiner*—James R. Feyrer

*Attorney, Agent, or Firm*—Oblon, Spivak, McClelland, Maier, & Neustadt, P.C.

[57] ABSTRACT

An improved bermudagrass plant, having superior properties, suitable for a variety of turf applications, is disclosed. The bermudagrass is characterized by a dark green color, high-shot density, low seed-head density, medium-course leaf texture, good fall color retention, average sod strength, good cold tolerance, excellent shade tolerance as compared to other bermudagrasses, some dollar spot, and average leaf-spot resistance.

1 Drawing Sheet

BACKGROUND OF THE NEW PLANT

The present invention relates to a new and distinct variety of bermudagrass, which has excellent turfgrass quality, good pest resistance and above-average environmental stress hardiness. The inventive bermudagrass is suitable for use on residential lawns, sport's fields, gold fairways and tees.

The inventive bermudagrass is characterized by a dark green color, high-shoot density, low seed-head density, medium-coarse leaf texture, good fall color retention, average sod strength, good cold tolerance, excellent shade tolerance as compared to other bermuda grasses, some dollar spot and average leaf-spot resistance.

BRIEF DESCRIPTION OF THE FIGURES

The plant is ilustrated in FIGS. 1–6, which are color photographs of the inventive bermudagrass.

Figure 1:
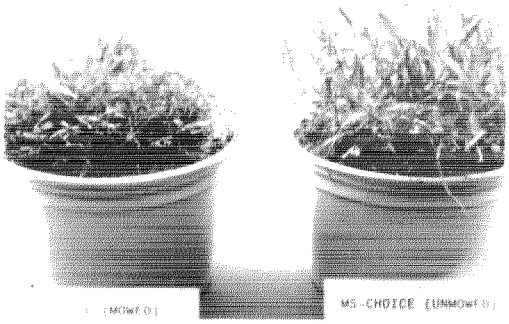
FIG. 1 reflects whole plant features of mowed and unmowed turf.

MS-Choice (experimental name MSB-30) is a distinct genotype of *Cynodon dactylon* Pers. that was developed and is vegatatively propagated at the Plant Science Research Center, Mississippi Agricultural and Forestry Experiment Station, Mississippi State, Miss. MS-Choice originated from a single clone collected from the 13th fairway at the Shady Oaks Country Club, Jackson, Miss. on Aug. 21, 1980. Persons knowledgeable of Shady Oaks Country Club's history said that this fairway was established with bermudagrass seed in 1913, has existed as a golf fairway since its original planting, and had not been intentionally replanted with bermudagrass seed, sprigs, plugs or sod since 1913.

MS-Choice's origin may be from any one of the following sources: (a) a seed within the original seed lot; (b) a seed or plant introduced unintentionally to this site; or (c) a plant which developed as a result of an environmentally selected mutation(s).

The identifying features of the original clone of MS-Choice were a dark green color, high shoot density, and lack of seed heads. The size of the original clone was approximately 3 ft in diameter. A 4 inch diameter plug was removed from the center of the clone and transplanted to a bermudagrass nursery located at the Plant Science Research Center. MS-Choice was 1 of 72 ecotypes of bermudagrass planted and maintained in this nursery.

MS-Choice was evaluated for 5 years in this nursery. During this period, MS-Choice maintained its original dark green color, high shoot density, and low seed head density. During this time no significant loss of MS-Choice turf was noticed due to pest or environmental stresses.

In 1986, MS-Choice was included in a regional bermudagrass evaluation trail located at 15 sites encompassing 11 states. Data was collected from 1986 to 1990. The findings from this study confirmed MS-Choice's dark green color, high shoot density, and low seed head density. In addition, MS-Choice was found to have moderate cold tolerance, excellent shade tolerance, good dollar spot and good leaf-spot resistance, and high turfgrass quality scores at all 15 field plot locations.

Morphological description: MS-Choice has a wide leaf width (2.2 to 2.6 mm), short leaf length (16.9 to 28.3 mm), medium internode length (7.2 to 13.2 mm), large internode (1.26 to 1.87 mm) and node diameter (1.43 to 1.87 mm) (Table 1).

Seed head density: The seed head density of MS-Choice was measured at 3 location for 2 or 3 years depending on location (Table 2). At all three location, MS-Choice showed very low seed head density that ranked well below the average when compared to the other bermudagrasses tested.

Genetic color: The genetic color of MS-Choice was visually rated at 7 locations for 1 or 2 years depending on location (Table 3). At all locations, MS-Choice's color was rated dark green. The stolons are light green and rhizomes are white.

The color designation of MS-Choice is 7.5 GY 3/4 using a Munsell color chart rating.

Shoot density: The shoot density of MS-Choice was measured at 2 location for 1 or 2 years depending on location (Table 4). MS-Choice has a high shoot density that ranked at the highest density compared to the other bermudagrasses tested.

Shade tolerance: The shade tolerance of MS-Choice was measured at 1 location for 2 years (Table 5). MS-Choice has a excellent tolerance to shade that ranked highest compared to the other bermudagrasses tested.

Ploidy level and chromosome number: MS-Choice's ploidy level and chromosome number were determined and compared to other bermudagrasses (Table 6). MS-Choice is a tetraploid with 36 chromosomes.

Turfgrass quality rating: The overall turf quality of MS-Choice was measured at 15 locations for 1, 2, or 3 years depending on location (Table 7). MS-Choice has excellent turfgrass quality. In comparison to other bermudagrasses tested, MS-Choice was at or near the top of the rankings.

Leaf texture: Leaf texture based on a visual comparison was measured at 8 locations for 1 or 2 years depending on location (Table 8). MS-Choice has a medium to course leaf texture.

Establishment rate: The establishment rate of MS-Choice was measured at scheduled intervals over a 54 day period after planting (Table 9). MS-Choice has a good establishment rate compared to the other bermudagrasses tested. At the end of the establishment period, MS-Choice had 98% turf cover.

Fall color retention: Fall color retention of MS-Choice was measured during the month of November at 6 locations for 1 or 3 years depending on location (Table 10). MS-Choice had good fall color retention that ranked at or slightly less than average when compared to the other bermudagrasses tested.

Unmowed height and sod strength: The unmowed height and sod strength of MS-Choice was measured at 1 location for 1 year and 1 location for 2 years, respectively (Table 11). MS-Choice had a low unmowed height and average sod strength compared to the other bermudagrasses tested.

Low temperature kill: The low temperature kill of MS-Choice was measured at 1 location for 2 consecutive years (Table 12). During both years, MS-Choice showed better than average low temperature tolerance compared to the other bermudagrasses tested.

Disease resistance: MS-Choice's resistance to leafspot (Helminthosporium spp.) and dollar spot (Sclerotinia spp.) was measured at 1 location for 1 or 2 years depending on location (Table 13). MS-Choice showed average resistance to leafspot and higher than average susceptibility to dollar spot compared to other bermudagrasses tested.

DISTINGUISHING FEATURES OF MS-CHOICE

Figure 2:
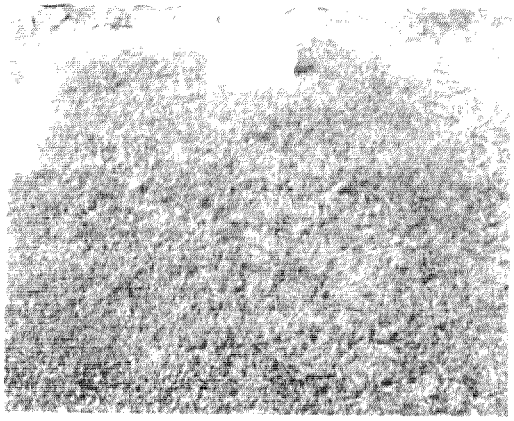
FIG. 2 is a photograph of a field plot of mowed turf.
Figure 3:
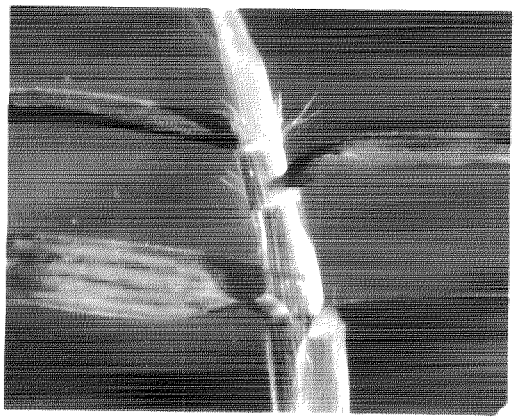
FIG. 3 is a photograph of a typical inflorescence structure showing three racemes per stalk.
Figure 4:
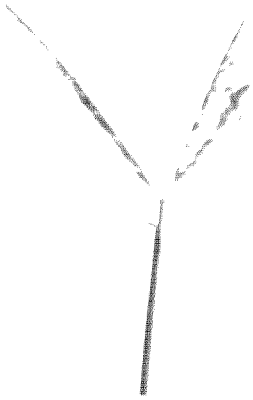
FIG. 4 is a photograph reflecting the leaf blade and sheath features of the inventive plant.
Figure 5:
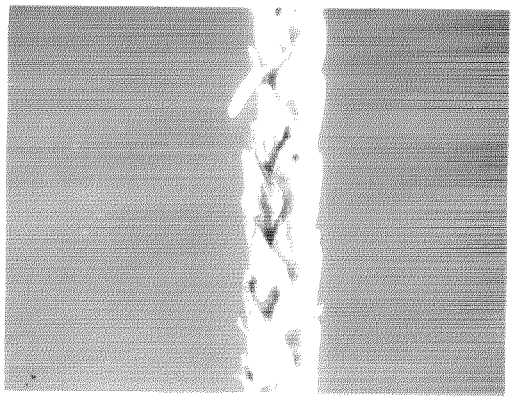
FIG. 5 is a photograph reflecting an abaxial view of spikelets of the inventive bermudagrass.
Figure 6:
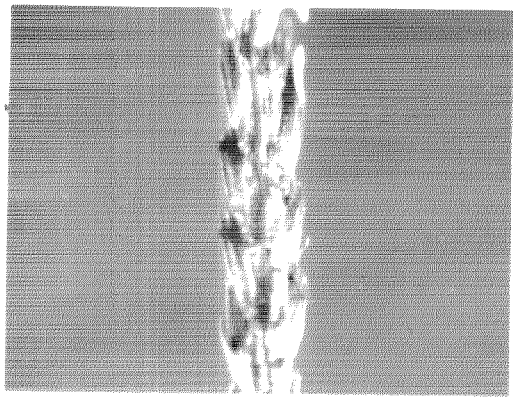
FIG. 6 is a photograph reflecting an adaxial view of spikelets of the inventive bermudagrass.

MS-Choice can be distinguished by morphological and turf performance characteristics. MS-Choice has high turf density and excellent turfgrass quality as illustrated in pot and field plot culture (FIGS. 1 and 2). MS-Choice's shoot structure is pilose on the abaxial and adaxial leaf blade surfaces, pubescence tufted at the ligule margins, and glabrous on the adaxial leaf surface and sheath (FIG. 4). MS-Choice has a raceme inflorescence structure with 3 racemes attached per stalk in a single whorl (FIG. 3). Spikelet density is medium with attachment spaced every 1.27 mm along the raceme. Length of an average spikelet is 2.3 mm with glumes extending ⅓ to ½ the length of a floret (FIGS. 5 and 6). The flower of MS-Choice has a purple stigma and yellow anthers.

MS-Choice has significantly wider leaves than MS-Pride, Tifgreen, Tifway II, and Tifway have (Table 1). The leaf length of MS-Choice is significantly shorter than Midiron and Tufcote. There were little differences in internode length between MS-Choice and the other bermudagrasses tested; however, the internode diameter was significantly larger than all bermudagrasses tested except Texturf 10. Node diameter of MS-Choice was significantly larger than all other bermudagrasses tested.

MS-Choice has turf performance characteristics that distinguish it from other bermudagrasses. Compared to all other bermudagrasses tested, MS-Choice showed significantly darker green color (Table 3), lower seed head density (Table 2), and greater shade tolerance (Table 5). Dark green color, low seed head density, and good shade tolerance are key features that make MS-Choice a highly desirable turfgrass.

MS-Choice, like all turf grasses, has a tendency to thatch. The tendency to thatch in this grass is limited. The thatch is comprised of dead leaves, dead or living stolons snd dead or living crowns. In contrast to other bermudagrasses, MS-Choice has a greather than average tendency to thatch.

The mowing height range for MS-Choice is from ½–2 inches. This bermudagrass may not be suitable for use for golf putting greens.

This grass although tetraploid, produce few seed-heads. An examination of the seed-heads showed the pollen to be non-viable, making it highly probable that the ovules are non-viable as well. The frequency of seed-heads is on the order of 2–3/100 $ft^2$. Given the outcrossing nature of this bermudagrass, there is virtually no practical chance of seed contaminating MS-Choice.

Additional performance characteristics of MS-Choice ranked above average compared to the others grasses tested. Some of these qualities of MS-Choice were high turf quality, shoot density good fall color retention, and moderate disease resistance.

The following additional distinctive characteristics are noted:

a) Leaf color is forest green and rated a 7.5 GY 3/4 based on a Munsell® color chart for plant tissue. There is no anthocyanin pigmentation expressed in leaves during the fall. The average leaf width is 2.4 mm and average length 22.6 mm.

b) The grass spreads by stolons and rhizomes and has a hightly compact, prostrate leaf canopy. Stolon color is 5 GY 5/8 based on a Munsell® color chart for plant tissue. There is no anthocyanin pigmentation expressed in stolons during the fall. The average stolon internode diameter is 1.43 mm, the average stolon node diameter is 1.65 mm, and average stolon internode length is 22.6 mm.

c) The grass has an extensive fibrous root system initiated from the nodes of stolons and rhizomes.

d) Leaves are folded in the bud shoot; the blades are mostly flat or slightly V-shaped with only the midvein visible; and the leaf tip is tapered to an acute apex.

e) The grass has a very low frequency of inflorescence formation having an average density of <1 inflorescence per square meter. Average height of culms is 38 mm. The fluorescence consists of 2 to 3 digitate spikes at the top of the main stem, folded down at a 30 to 40 degree angle from verticle, spikelets sessiled and closely appressed. The average length of a spike is 16 mm.

f) The grass blade is pilose on the adaxial and abaxial surface. The ligule consists of a fringe of hairs. The sheath is glabrous, split with margins overlapping, and pubescence tufted at the side of the ligule. The collar is a continuous narrow band, glabrous and auricles are absent.

g) The spikelets are glabrous in two rows, blunt at their base and pointed at their tips. Spikelets are attached an average distance of 1.27 mm along the spikes. The length of an average spikelet is 2.3 mm with glumes extending ⅓ to ½ the length of a floret. The spikelet has stigmas of dark purple-red color rated as a 5 RP 3/10 based on a Munsell® color chart for plant tissue.

h) The grass has a somatic chromosome number of 36 and classed as a tetraploid.

TABLE 1

A quantitative comparison of morphological features for describing the whole plant morphology of MS-Choice and eight other bermudagrasses.

| Bermudagrass Entry | Leaf Width | Leaf Length | Internode Length | Internode Diameter | Node Diameter |
|---|---|---|---|---|---|
| | ----------mm---------- | | | | |
| MS-Choice | 2.4 | 22.6 | 10.2 | 1.43 | 1.65 |
| Midiron | 2.3 | 35.8 | 15.7 | 1.00 | 1.35 |
| Texturf 10 | 1.8 | 22.9 | 9.4 | 1.28 | 1.28 |
| Turfcote | 1.7 | 33.7 | 12.9 | 1.10 | 1.33 |
| MS-Express | 1.8 | 23.8 | 11.1 | 0.95 | 1.25 |
| Tifgreen | 1.3 | 22.3 | 9.4 | 0.90 | 1.22 |
| TIfway II | 1.3 | 27.2 | 10.9 | 0.64 | 0.85 |
| MS-Pride | 1.3 | 29.0 | 11.8 | 0.65 | 0.85 |
| Tifway | 1.2 | 28.2 | 11.8 | 0.67 | 0.89 |
| LSD (.05) | .22 | 5.66 | 3.02 | 0.172 | 0.22 |
| Mean | 1.65 | 27.27 | 11.47 | 0.93 | 1.18 |

TABLE 2

Comparative seed head density of MS-Choice and nine other bermudgrasses.

| | Field Plot Locations | | |
|---|---|---|---|
| Bermudagrass Entry | Starkville Mississippi | Las Cruces New Mexico | Blacksburg Virginia |
| MS-Choice | 8.8[1] | 9.0 | 9.0 |
| Tifgreen | 4.0 | 4.7 | 6.2 |
| Tifway | 7.0 | 7.8 | 8.2 |
| Tifway II | 7.3 | 7.8 | 7.8 |
| Texturf 10 | 5.3 | 8.0 | 6.7 |
| Tufcote | 7.5 | 5.3 | 7.7 |
| Midiron | 5.7 | 5.0 | 7.3 |
| MS-Pride | 7.3 | 7.9 | 7.7 |
| MS-Express | 4.3 | 5.1 | 6.5 |
| Arizona Common | 4.7 | 5.9 | 6.7 |
| LSD (.05) | 0.77 | 0.67 | 0.82 |
| Mean | 6.2 | 6.6 | 7.4 |
| Cultivar × Year interaction. | * | ** | ** |

TABLE 2-continued

Comparative seed head density of MS-Choice and nine other bermudgrasses.

| | Field Plot Locations | | |
|---|---|---|---|
| Bermudagrass Entry | Starkville Mississippi | Las Cruces New Mexico | Blacksburg Virginia |
| Years data was collected. | 1987 1988 | 1986 1987 1988 | 1987 1988 |

[1]Seed head density rating based on a 1 to 9 scale; with 1 = high seed head density and 9 = no seed heads.

*, **Significant at the .05 and .01 level of probability, respectively.

TABLE 3

Comparative genetic color of MS-Choice and nine other bermudagrasses.

| | Field Plot Location | | | |
|---|---|---|---|---|
| Bermudgrass Entry | Tucson Arizona | Santa Ana California | Gainsville Florida | Starkville Mississippi |
| MS-Choice | 7.0[1] | 9.0 | 7.3 | 7.7 |
| Tifgreen | 6.3 | 7.0 | 5.2 | 5.0 |
| Tifway | 6.7 | 8.0 | 7.0 | 6.3 |
| Tifway II | 6.3 | 8.0 | 6.8 | 7.0 |
| Texturf 10 | 6.3 | 7.7 | 5.8 | 5.3 |
| Tufcote | 6.7 | 6.7 | 5.8 | 5.0 |
| Midiron | 6.7 | 7.7 | 5.7 | 5.3 |
| MS-Pride | 6.0 | 7.7 | 6.8 | 7.0 |
| MS-Express | 6.3 | 7.7 | 6.2 | 5.0 |
| Arizona Common | 5.3 | 5.7 | 5.2 | 5.0 |
| LSD (.05) | NS | 0.75 | 0.55 | 0.65 |
| Mean | 6.4 | 7.5 | 6.2 | 5.9 |
| Cultivar × Year interaction. | | | ** | |
| Years data was collected. | 1987 | 1987 | 1987 1988 | 1988 |

| | Field Plot Location | | |
|---|---|---|---|
| Bermudagrass Entry | Las Cruces New Mexico | Stillwater Oklahoma | Cleveland Texas |
| MS-Choice | 7.5 | 8.0 | 8.7 |
| Tifgreen | 6.8 | 6.3 | 7.7 |
| Tifway | 7.0 | 7.7 | 9.0 |
| Tifway II | 7.7 | 6.0 | 8.0 |
| Texturf 10 | 7.0 | 7.3 | 8.0 |
| Tufcote | 7.2 | 4.7 | 7.3 |
| Midiron | 6.3 | 6.7 | 7.0 |
| MS-Pride | 7.7 | 7.0 | 8.7 |
| MS-Express | 6.7 | 6.3 | 7.7 |
| Arizona Common | 5.5 | 6.0 | 6.7 |
| LSD (.05) | NS | 1.08 | 0.80 |
| Mean | 6.9 | 6.6 | 7.9 |
| Cultivar × Year interaction. | NS | | |
| Years data was collected. | 1986 1987 | 1988 | 1988 |

[1]Genetic color rating based on a 1 to 9 scale; with 1 = light green color and 9 = dark green color.

*, **Significant at the .05 and .01 level of probability, respectively.

TABLE 4

Comparative shoot density of MS-Choice and nine other bermudagrasses.

| Bermudagrass Entry | Field Plot Location: Las Cruces New Mexico | Stillwater Oklahoma |
|---|---|---|
| MS-Choice | 8.4[1] | 8.0 |
| Tifgreen | 8.4 | 7.7 |
| MS-Pride | 8.1 | 7.3 |
| Texturf 10 | 7.8 | 8.0 |
| Tifway | 7.7 | 7.7 |
| Midiron | 7.9 | 7.0 |
| Tifway II | 7.3 | 7.7 |
| MS-Express | 7.3 | 7.3 |
| Tufcote | 6.3 | 7.7 |
| Arizona Common | 3.9 | 6.0 |
| LSD (0.05) | 0.61 | 0.95 |
| Mean | 7.3 | 7.5 |
| Entry × Year Interaction | ** | NA |
| Year(s) data was recorded | 1986 1987 | 1987 |

[1]Shoot density rating based on a visual scale; with 1 = low density and 9 = high density.
*, **Significant at the 0.05 and 0.01 level of probability, respectively.

TABLE 5

Comparative shade tolerance of MS-Choice and nine other bermudgrasses[1].

| Bermudagrass Entry | Shade Tolerance |
|---|---|
| MS-Choice | 4.9[2] |
| MS-Pride | 4.5 |
| Tifgreen | 4.3 |
| MS-Express | 4.3 |
| Tifway II | 3.8 |
| Tifway | 3.7 |
| Texturf 10 | 3.5 |
| Tufcote | 3.4 |
| Arizona Common | 2.5 |
| Midiron | 2.1 |
| LSD (0.05) | 0.39 |
| Mean | 3.7 |
| Cultivar × Year interaction | ** |
| Years data was collected | 1987 1988 |

[1]Field plots located in Starkville, MS.
[2]Shade tolerance based on a visual scale of 1 to 9; with 9 = excellent shade tolerance and 1 = poor shade tolerance.
*, **Significant at the 0.05 and 0.01 level of probability, respectively.

TABLE 6

The ploidy level and chromosome number of MS-Choice and nine other bermudagrasses.

| Bermudagrass Entry | Ploidy Level | Chromosome Number |
|---|---|---|
| MS-Choice | Tetraploid | 36[1] |
| Texturf 10 | | 36 |
| Turfcote | | 36 |
| Midiron | | 36 |
| Arizona Common | | 36 |
| MS-Express | Triploid | 27 |
| MS-Pride | | 27 |
| Tifgreen | | 27 |

TABLE 6-continued

The ploidy level and chromosome number of MS-Choice and nine other bermudagrasses.

| Bermudagrass Entry | Ploidy Level | Chromosome Number |
|---|---|---|
| Tifway | | 27 |
| Tifway II | | 27 |

[1]Chromosome numbers were determined using squashes of root tips.

TABLE 7

Comparative turfgrass quality of MS-Choice and nine other bermudagrasses.

| Bermudagrass Entry | Field Plot Location: Tucson Arizona | Santa Ana California | Riverside California | Gainsville Florida |
|---|---|---|---|---|
| MS-Choice | 7.5[1] | 6.3 | 4.9 | 5.7 |
| Tifgreen | 7.3 | 5.8 | 5.4 | 4.8 |
| Tifway | 7.8 | 6.5 | 5.5 | 5.8 |
| Tifway II | 7.9 | 6.5 | 5.7 | 5.7 |
| Texturf 10 | 7.8 | 5.8 | 5.1 | 5.1 |
| Tufcote | 7.3 | 5.4 | 5.2 | 5.6 |
| Midiron | 6.2 | 5.8 | 4.9 | 4.9 |
| MS-Pride | 8.3 | 6.5 | 5.3 | 6.0 |
| MS-Express | 7.8 | 5.9 | 5.8 | 5.2 |
| Arizona Common | 5.5 | 4.4 | 4.7 | 4.9 |
| LSD (.05) | 0.54 | 0.33 | 0.55 | 0.32 |
| Mean | 7.3 | 5.9 | 5.2 | 5.4 |
| Cultivar × Year interaction. | | ** | NS | ** |
| Year(s) data was collected. | 1988 | 1986 1987 | 1986 1987 1988 | 1987 1988 1988 |

| Bermudagrass Entry | Field Plot Location: Manhattan Kansas | Wichita Kansas | Baton Rogue Louisiana | Silver Springs Maryland |
|---|---|---|---|---|
| MS-Choice | 6.9 | 8.0 | 7.0 | 6.0 |
| Tifgreen | 6.9 | 7.8 | 7.7 | 6.2 |
| Tifway | 6.3 | 8.2 | 7.6 | 6.3 |
| Tifway II | 6.5 | 8.4 | 7.6 | 6.4 |
| Texturf 10 | 6.7 | 7.9 | 6.9 | 5.3 |
| Tufcote | 6.9 | 7.7 | 7.3 | 5.8 |
| Midiron | 6.7 | 7.7 | 6.7 | 5.4 |
| MS-Pride | 6.5 | 8.3 | 7.5 | 6.4 |
| MS-Express | 6.8 | 8.1 | 7.6 | 7.7 |
| Arizona Common | 5.0 | 5.9 | 6.3 | 5.0 |
| LSD (.05) | 0.38 | 0.30 | 0.59 | NS |
| Mean | 6.5 | 7.8 | 7.2 | 6.1 |
| Cultivar × Year interaction. | ** | ** | * | |
| Year(s) data was collected. | 1987 1988 | 1986 1987 | 1987 1988 1988 | 1988 |

| Bermudagrass Entry | Field Plot Location: Starkville Mississippi | Las Cruces New Mexico | Cleveland Texas | Beltsville Maryland |
|---|---|---|---|---|
| MS-Choice | 6.1[1] | 7.3 | 8.0 | 7.0 |
| Tifgreen | 7.4 | 6.3 | 9.0 | 7.3 |
| Tifway | 6.7 | 7.0 | 7.7 | 6.6 |
| Tifway II | 6.9 | 7.5 | 8.0 | 6.8 |
| Texturf 10 | 5.6 | 6.8 | 5.7 | 6.5 |
| Tufcote | 5.5 | 6.2 | 5.7 | 6.7 |
| Midiron | 5.1 | 6.5 | 5.3 | 5.8 |
| MS-Pride | 6.9 | 7.2 | 8.0 | 6.9 |
| MS-Express | 7.6 | 6.7 | 8.7 | 7.0 |
| Arizona Common | 4.1 | 3.8 | 4.0 | 4.5 |

TABLE 7-continued

| | | | | |
|---|---|---|---|---|
| LSD (.05) | 0.19 | 0.49 | 1.14 | 0.38 |
| Mean | 6.2 | 6.5 | 7.0 | 6.5 |
| Cultivar × Year interaction. | ** | ** | NA | ** |
| Year(s) data was collected. | 1986<br>1987<br>1988 | 1986<br>1987<br>1988 | 1988 | 1986<br>1987<br>1988 |

| Bermudagrass Entry | Field Plot Location<br>Blacksburg Virginia | Blackstone Virginia | Virginia Beach Virginia |
|---|---|---|---|
| MS-Choice | 5.9 | 6.8 | 6.7 |
| Tifgreen | 5.9 | 6.8 | 6.2 |
| Tifway | 6.5 | 7.0 | 6.3 |
| Tifway II | 6.1 | 6.8 | 6.9 |
| Texturf 10 | 6.0 | 6.6 | 5.7 |
| Tufcote | 5.8 | 6.4 | 4.9 |
| Midiron | 5.0 | 5.8 | 5.9 |
| MS-Pride | 5.8 | 6.8 | 6.4 |
| MS-Express | 6.5 | 6.8 | 6.0 |
| Arizona Common | 4.2 | 5.0 | 3.9 |
| LSD (.05) | 0.43 | 0.38 | 0.77 |
| Mean | 5.8 | 6.5 | 5.9 |
| Cultivar × Year interaction. | * | ** | NA |
| Year(s) data was collected. | 1986<br>1987<br>1988 | 1986<br>1988 | 1986 |

[1]Turfgrass quality ratings based on a 1 to 9 scale with 1 = poor turfgrass quality and 9 = excellent turf quality.
*, **Significant at the .05 and .01 level of probability, respectively.

TABLE 8

Comparative leaf texture of MS-Choice and nine other bermudagrasses.

| Cultivar | Field Plot Locations<br>Tucson Arizona | Wichita Kansas | Gainsville Florida | Starkville Mississippi |
|---|---|---|---|---|
| MS-Choice | 5.3[1] | 6.7 | 5.7 | 5.0 |
| Tifgreen | 7.3 | 9.0 | 7.5 | 7.7 |
| Tifway | 7.0 | 7.7 | 7.8 | 6.0 |
| Tifway II | 6.3 | 8.3 | 8.2 | 6.0 |
| Texturf 10 | 5.7 | 8.0 | 5.5 | 5.0 |
| Tufcote | 5.7 | 6.0 | 7.0 | 5.0 |
| Midiron | 5.3 | 4.0 | 5.8 | 5.0 |
| MS-Pride | 6.7 | 7.3 | 8.0 | 6.0 |
| MS-Express | 7.7 | 9.0 | 7.3 | 8.0 |
| Arizona Common | 4.3 | 3.7 | 2.7 | 4.3 |
| LSD (.05) | 0.92 | 0.68 | 1.01 | 0.43 |
| Mean | 6.1 | 7.0 | 6.6 | 5.8 |
| Cultivar × Year interaction. | | | ** | |
| Year(s) data was collected. | 1987 | 1986 | 1987<br>1988 | 1988 |

| Cultivar | Field Plot Locations<br>Las Cruces New Mexico | Baton Rogue Louisiana | Virignia Beach Virginia |
|---|---|---|---|
| MS-Choice | 6.5 | 6.3 | 4.7 |
| Tifgreen | 9.0 | 9.0 | 7.0 |
| Tifway | 8.2 | 9.0 | 6.0 |
| Tifway II | 8.3 | 9.0 | 5.7 |
| Texturf 10 | 5.8 | 6.3 | 5.7 |
| Tufcote | 6.7 | 9.0 | 3.7 |
| Midiron | 6.8 | 7.7 | 4.3 |
| MS-Pride | 8.5 | 9.0 | 6.0 |
| MS-Express | 8.8 | 9.0 | 6.0 |
| Arizona Common | 4.2 | 6.3 | 2.3 |
| LSD (.05) | 0.79 | 0.79 | 1.19 |

TABLE 8-continued

| | | | | |
|---|---|---|---|---|
| Mean | 7.3 | 8.1 | 5.1 | |
| Cultivar × Year interaction. | ** | | | |
| Year(s) data was collected. | 1986<br>1987 | 1988 | 1988 | 1986 |

[1]Leaf texture rating based on a 1 to 9 scale; with 1 = coarse leaf texture and 9 = fine leaf texture.
*, **Significant at the 0.05 and 0.01 level of probability, respectively.

TABLE 9

Comparative establishment rate of MS-Choice and nine other bermudagrasses.

| Bermudagrass Entry | Days After Planting[1]<br>26 | 33 | 40 | 47 | 54 |
|---|---|---|---|---|---|
| | ----------% cover---------- | | | | |
| Arizona Common | 65.0[2] | 66.7 | 90.0 | 97.7 | 100.0 |
| Midiron | 36.7 | 43.3 | 76.7 | 91.7 | 100.0 |
| MS-Choice | 36.7 | 38.3 | 71.7 | 88.3 | 100.0 |
| Tifgreen | 35.0 | 41.7 | 80.0 | 91.7 | 100.0 |
| MS-Express | 35.3 | 45.0 | 86.7 | 88.3 | 98.3 |
| Tufcote | 35.0 | 40.0 | 76.7 | 91.0 | 98.3 |
| Texturf 10 | 31.7 | 43.3 | 73.3 | 88.3 | 98.3 |
| Tifway | 25.0 | 30.0 | 51.7 | 66.7 | 93.3 |
| Tifway II | 21.7 | 28.3 | 41.7 | 73.3 | 93.3 |
| MS-Pride | 20.0 | 28.3 | 51.7 | 66.7 | 91.7 |
| LSD (0.05) | 14.3 | 14.7 | 18.7 | 20.3 | 8.2 |
| Mean | 34.2 | 40.5 | 70.0 | 84.4 | 97.3 |

[1]All entries were planted on 6-20-86 using 2 inch diameter plugs spaced on 1 ft intervals. Plots were located in Starkville, MS and plot size was 5 × 10 ft.
[2]The % cover was based on a visual estimation of the % of the plot area covered by vegetation.

TABLE 10

Comparative fall color retention of MS-Choice and nine other bermudgrasses.

| Bermudagrasses Entry | Field Plot Location<br>Beltsville Maryland | Raleigh North Carolina | Starkville Mississippi | Las Cruces New Mexico | Loc. 2 New Mexico |
|---|---|---|---|---|---|
| MS-Pride | 5.3[1] | 6.7 | 6.5 | 4.3 | 5.3 |
| Tifway | 4.8 | 6.7 | 6.2 | 4.6 | 5.7 |
| Tifway II | 4.5 | 7.3 | 6.5 | 4.4 | 5.7 |
| Tufcote | 2.8 | 6.3 | 5.3 | 3.2 | 3.3 |
| Midiron | 2.3 | 3.7 | 4.2 | 3.1 | 3.3 |
| Texturf 10 | 2.2 | 5.3 | 3.2 | 2.6 | 5.0 |
| MS-Choice | 2.0 | 5.7 | 4.2 | 3.4 | 4.3 |
| Tifgreen | 2.0 | 6.3 | 3.2 | 2.0 | 4.0 |
| MS-Express | 1.7 | 6.7 | 3.0 | 2.1 | 4.3 |
| Arizona Common | 1.7 | 5.7 | 4.5 | 3.4 | 2.3 |
| LSD (0.05) | 0.68 | 1.54 | 0.43 | 0.76 | 1.74 |
| Mean | 2.9 | 6.0 | 4.7 | 3.3 | 4.3 |
| Cultivar × Year interaction | ** | NA | ** | ** | NA |
| Year(s) data was collected | 1986<br>1987 | 1986 | 1986<br>1988 | 1986<br>1987<br>1988 | 1988 |

[1]Color ratings based on a visual scale of color with; 9 = green color and 1 = brown color.
*, **Significant at the 0.05 and 0.01 level of probability, respectively.

TABLE 11

Comparative height of unmowed plots and sod strength of MS-Choice and nine other bermudagrasses.

| Bermudagrass Entry | Plant Measurement: Unmowed Height | Sod Strength |
|---|---|---|
| | --cm-- | --lbs-- |
| Arizona Common | 31.7[1] | 26.8[2] |
| Tufcote | 8.7 | 39.3 |
| Midiron | 5.7 | 39.5 |
| Tifway II | 5.0 | 121.5 |
| MS-Choice | 4.3 | 65.5 |
| Texturf 10 | 4.3 | 77.8 |
| Tifway | 4.3 | 95.2 |
| MS-Express | 4.0 | 86.7 |
| MS-Pride | 4.0 | 157.7 |
| Tifgreen | 3.3 | 74.7 |
| LSD (0.05) | 1.8 | 34.5 |
| Mean | 7.5 | 78.5 |
| Entry × Year Interaction | NA | NS |
| Year(s) data was collected | 1986 | 1987<br>1988 |
| Location | Las Cruces New Mexico | Starkville Mississippi |

[1]The shoot height was determined by measuring the height of the grass at its maximum length above the soil surface.
[2]Sod strength was determined by measuring the amount of force (lbs) required to shear an 18 × 24 × 1" section of sod.

TABLE 12

Comparative turf mortality due to winter kill of MS-Choice and nine other bermudagrasses[1].

| Bermudagrass Entry | Year: 1987 | 1988 |
|---|---|---|
| | ---% turf mortality--- | |
| Tufcote | 0[2] | 0 |
| Tifgreen | 3.3 | 1.7 |
| MS-Express | 1.7 | 5.0 |
| Texturf 10 | 3.3 | 10.0 |
| MS-Pride | 5.0 | 25.0 |
| Midiron | 11.7 | 11.7 |
| Tifway | 5.0 | 36.7 |
| Tifway II | 5.0 | 36.7 |
| MS-Choice | 11.7 | 36.7 |
| Arizona Common | 35.0 | 88.3 |

TABLE 12-continued

Comparative turf mortality due to winter kill of MS-Choice and nine other bermudagrasses[1].

| Bermudagrass Entry | Year: 1987 | 1988 |
|---|---|---|
| LSD (0.05) | 11.6 | 12.9 |
| Mean | 8.2 | 25.2 |

[1]Field plot were located in Beltsville, MD.
[2]The % of plot area lost to low temperature killed was based on a visual evaluation of turf lost immediately following spring green-up in May.

TABLE 13

Comparative leafspot (Helminthosporium spp.) and dollarspot (Sclerotinia spp.) disease resistance of MS-Choice and nine other bermudagrasses.

| Bermudagrass Entry | Disease Rating: Helminthosporium | Dollar Spot |
|---|---|---|
| MS-Pride | 8.8[1] | 8.4 |
| MS-Express | 8.7 | 7.7 |
| Tifgreen | 8.3 | 7.3 |
| Tifway II | 8.3 | 8.5 |
| Texturf 10 | 8.2 | 8.7 |
| Tifway | 8.2 | 8.7 |
| MS-Choice | 7.9 | 6.4 |
| Midiron | 7.8 | 8.7 |
| Tufcote | 7.0 | 8.8 |
| Arizona Common | 6.2 | 8.6 |
| LSD (0.05) | 0.73 | 0.83 |
| Mean | 7.9 | 8.2 |
| Entry × Year Interaction | ** | ** |
| Year(s) data was collected | 1986<br>1988 | 1986<br>1988 |

[1]Disease rating based on a visual scale of 1 to 9; with 9 = no disease damage (excellent disease resistance) and 1 = high incidence of disease damage (poor disease resistance).
*, **Significant at the 0.05 and 0.01 level of probability, respectively.

What is claimed is:

1. A bermudagrass plant substantially as described and illustrated in the specification herein.

* * * * *

UNITED STATES PATENT AND TRADEMARK OFFICE

CERTIFICATE OF CORRECTION

PATENT NO. : Plant 10,332

DATED : April 14, 1998

INVENTOR(S) : Jeffrey V. KRANS, et al.

It is certified that error appears in the above-identified patent and that said Letters Patent is hereby corrected as shown below:

On the title page, item [73], the assignee's address should be:

--Mississippi State, Mississippi--

Signed and Sealed this

FourthDay of August, 1998

Bruce Lehman

*Attest:*

BRUCE LEHMAN

*Attesting Officer*

*Commissioner of Patents and Trademarks*